US010524746B2

(12) United States Patent
Maruta

(10) Patent No.: US 10,524,746 B2
(45) Date of Patent: Jan. 7, 2020

(54) RADIATION IMAGE CAPTURING SYSTEM

(71) Applicant: Konica Minolta, Inc., Chiyoda-ku, Tokyo (JP)

(72) Inventor: Yuuichi Maruta, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 119 days.

(21) Appl. No.: 15/916,747

(22) Filed: Mar. 9, 2018

(65) Prior Publication Data
US 2018/0256123 A1 Sep. 13, 2018

(30) Foreign Application Priority Data
Mar. 13, 2017 (JP) .................................. 2017-046918

(51) Int. Cl.
*A61B 6/00* (2006.01)
*G01T 1/24* (2006.01)

(52) U.S. Cl.
CPC ............ *A61B 6/4283* (2013.01); *G01T 1/247* (2013.01); *A61B 6/4233* (2013.01)

(58) Field of Classification Search
CPC ..... A61B 6/4233; A61B 6/4283; A61B 6/542; G01T 1/247
See application file for complete search history.

(56) References Cited

U.S. PATENT DOCUMENTS

| 6,324,249 | B1* | 11/2001 | Fazzio | G01N 23/04 378/22 |
| 2010/0080438 | A1* | 4/2010 | Nishimura | G06T 11/005 382/132 |
| 2011/0170669 | A1* | 7/2011 | Nakatsugawa | A61B 6/102 378/116 |
| 2014/0110595 | A1* | 4/2014 | Iwakiri | A61B 6/4233 250/394 |
| 2014/0254760 | A1* | 9/2014 | Hiroike | A61B 6/4233 378/62 |

FOREIGN PATENT DOCUMENTS

JP 6034786 B2 11/2016

* cited by examiner

*Primary Examiner* — Marcus H Taningco
(74) *Attorney, Agent, or Firm* — Cantor Colburn LLP

(57) ABSTRACT

A radiation image capturing system includes the following. A radiation irradiating apparatus irradiates the radiation image capturing apparatus according to control by a generator. A control device transmits an external synchronizing signal to the radiation image capturing apparatus, transmits an irradiating request signal to the generator, and synchronizes the radiation image capturing apparatus with the radiation irradiating apparatus. When the external synchronizing signal is received, the radiation image capturing apparatus switches the control mode. After the control mode is switched, the radiation image capturing apparatus starts a readout process of the image data at a timing delayed a predetermined amount of time from a timing that the external synchronizing signal is received. The control device transmits the irradiating request signal to the generator at a timing delayed a predetermined amount of time from a timing that the irradiating request signal should be transmitted to the generator.

6 Claims, 13 Drawing Sheets

| | | | | | |
|---|---|---|---|---|---|
| L1 | D(1,1) | D(1,2) | D(1,3) | D(1,4) | D(1,5) |
| L2 | D(2,1) | D(2,2) | D(2,3) | D(2,4) | D(2,5) |
| L3 | D(3,1) | D(3,2) | D(3,3) | D(3,4) | D(3,5) |
| L4 | D(4,1) | D(4,2) | D(4,3) | D(4,4) | D(4,5) |
| L5 | D(5,1) | D(5,2) | D(5,3) | D(5,4) | D(5,5) |
| L6 | D(6,1) | D(6,2) | D(6,3) | D(6,4) | D(6,5) |
| L7 | D(7,1) | D(7,2) | D(7,3) | D(7,4) | D(7,5) |
| L8 | D(8,1) | D(8,2) | D(8,3) | D(8,4) | D(8,5) |
| L9 | D(9,1) | D(9,2) | D(9,3) | D(9,4) | D(9,5) |
| L10 | D(10,1) | D(10,2) | D(10,3) | D(10,4) | D(10,5) |
| L11 | D(11,1) | D(11,2) | D(11,3) | D(11,4) | D(11,5) |
| L12 | D(12,1) | D(12,2) | D(12,3) | D(12,4) | D(12,5) |

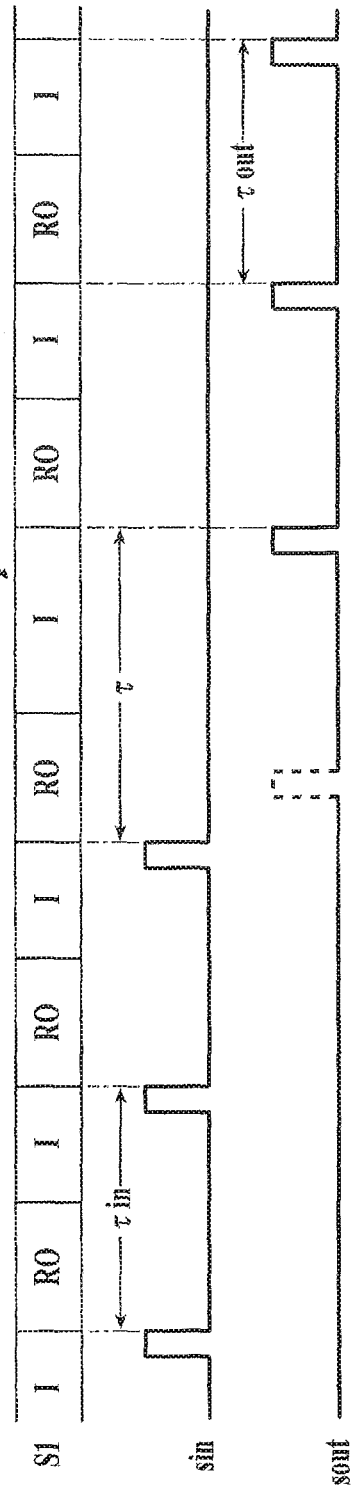
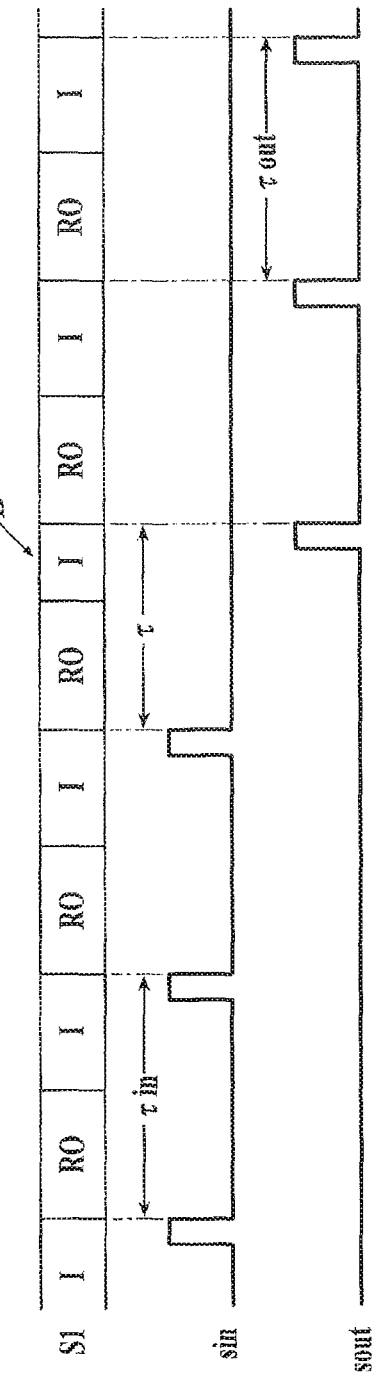
FIG.15A
FIG.15B

RADIATION IMAGE CAPTURING SYSTEM

CROSS-REFERENCE TO RELATED APPLICATIONS

The present application claims priority under 35 U.S.C. § 119 to Japanese Patent Application No. 2017-046918, filed on Mar. 13, 2017, the entire disclosure of which are incorporated herein by reference.

BACKGROUND

1. Technological Field

The present invention relates to a radiation image capturing system. Specifically, the present invention relates to a radiation image capturing system which irradiates radiation to a patient as a subject a plurality of times so as to be able to capture a moving image.

2. Description of the Related Art

There is a radiation image capturing apparatus (also called a flat panel detector, semiconductor image sensor, etc.) in which a plurality of radiation detecting elements are arranged two-dimensionally (in a matrix) and the radiation which passes through the subject is converted to image data according to the strength and detected by the radiation detecting elements (for each pixel). Conventionally, simple capturing was developed in which radiation is irradiated to the subject once and the radiation image capturing is performed.

However, the radiation image capturing apparatus is able to store the image data read out from the radiation detecting elements in the storage of the apparatus and is able to transfer the image data to external devices. Therefore, a technique is developed to irradiate radiation a plurality of times to the radiation image capturing apparatus and to capture the moving image of the capturing site of the patient as the subject.

For example, when the moving image is captured, radiation is irradiated a plurality of times to the chest of the patient who is the subject as the capturing site and each frame image is captured to perform movement capturing. For example, as shown in FIG. 13, in movement capturing, frame images of the lung field R of the patient at each time T (T=t0 to t6) can be obtained. The frame images can be analyzed to obtain maximum inspiratory level, maximum expiratory level of the lung field R, and inspiratory period and expiratory period. The frame images obtained by moving image capturing such as movement capturing can be further analyzed to be applied to diagnosis (for example, see Japanese Patent No. 6034786).

One method of performing such moving image capturing is the controller of the radiation image capturing apparatus emits a pulsed synchronizing signal to each functional unit such as a gate driver (this is called an internal synchronizing signal as a synchronizing signal generated in the radiation image capturing apparatus) and the internal synchronizing signal acts as a trigger so that the functional units operate synchronized with the internal synchronizing signal. With this, the functional units are synchronized to perform processes such as a readout process of the image data D from the radiation detecting elements. When the readout process of the image data D is performed each time the internal synchronizing signal is emitted, the plurality of frame images are captured.

The generator of the radiation irradiating apparatus which irradiates radiation to the radiation image capturing apparatus can generate a pulsed irradiating signal or an external control unit may transmit a pulsed irradiating request signal to the generator of the radiation irradiating apparatus. With this, the generator may repeatedly irradiate radiation from the radiation irradiating apparatus according to the irradiating signal or the irradiating request signal.

For example, if the radiation is irradiated from the radiation irradiating apparatus while the radiation image capturing apparatus performs the readout process of the image data D, the readout image data D becomes an abnormal value or the image data D read out in the next frame becomes an abnormal value. When capturing needs to be performed again due to the above problems, radiation exposure amount on the patient as the subject may increase more than necessary.

Therefore, according to the above configuration, for example, as shown in FIG. 14, a cycle $\tau$in of an internal synchronizing signal si in the radiation image capturing apparatus and a cycle $\tau$X of an irradiating signal sx emitted from the generator of the radiation irradiating apparatus are set to be the same cycle $\tau^*$. Alternatively, the cycle $\tau$in of the internal synchronizing signal sin in the radiation image capturing apparatus and a cycle $\tau$re of the irradiating request signal (the irradiating signal sx is emitted from the generator to the radiation irradiating apparatus according to the irradiating request signal sre) transmitted from the control unit to the generator are set to be the same cycle $\tau^*$. Then, the timing to emit the irradiating signal sx with the generator or the timing to transmit the irradiating request signal sre from the control unit to the generator is shifted from the timing to emit the internal synchronizing signal sin in the radiation image capturing apparatus at a predetermined time difference $\Delta\tau$. With this, for example, as shown in the later-described FIG. 9, the radiation is irradiated from the radiation irradiating apparatus while a state S1 of the radiation image capturing apparatus is a charge accumulating state I.

The diagonal lines in the drawings show the term that the radiation is irradiated. The charge accumulating state I is a state between a readout process RO of the image data D of one frame and the readout process RO of the image data D of the next frame. The charge accumulating state I is the state in which the charge generated by irradiating radiation can be accumulated in the radiation detecting elements. Therefore, the predetermined time difference $\Delta\tau$ needs to be adjusted so that the radiation is irradiated from the radiation irradiating apparatus to the radiation image capturing apparatus while the state S1 of the radiation image capturing apparatus is the charge accumulating state I.

According to the example shown in FIG. 14, the readout process RO of the image data D is started in the radiation image capturing apparatus synchronized with the falling of the internal synchronizing signal sin, and the readout process RO of the image data D is performed using a predetermined amount of time. The irradiation of radiation is started in the radiation irradiating apparatus synchronized with the rising of the irradiating signal sx or the irradiating request signal sre, and the radiation is irradiated for a set amount of irradiating time.

According to the above configuration, it is possible to prevent the following problems such as the radiation being irradiated from the radiation irradiating apparatus while the readout process RO of the image data D is performed in the radiation image capturing apparatus or due to the above, the recapturing becoming necessary and the amount of exposure on the patient as the subject increasing more than necessary.

However, even if the timing of emitting the irradiating signal sx with the generator of the radiation irradiating apparatus or the timing of transmitting the irradiating request signal sre from the control unit to the generator is adjusted before capturing so that the signals are emitted or transmitted delayed with a predetermined time difference $\Delta\tau$ from the timing that the internal synchronizing signal sin is emitted in the radiation image capturing apparatus as shown in FIG. 14 and as described above, the time is counted with timers separately provided in the radiation image capturing apparatus and the control unit. Therefore, small differences in the accuracy of the timer may accumulate and provide an influence. As the moving image capturing progresses, the time difference between the internal synchronizing signal sin and the irradiating request signal sre may gradually differ from the original time difference $\Delta\tau$. That is, the time difference $\Delta\tau$ may gradually increase or gradually decrease.

Therefore, there is still a possibility that the radiation is irradiated from the radiation irradiating apparatus while the readout process RO of the image data D is performed in the radiation image capturing apparatus. In order to avoid such situation, for example, it is possible to configure the radiation image capturing apparatus so that the internal synchronizing signal is not emitted, and the operation of the radiation image capturing apparatus and the operation of the generator of the radiation emitting apparatus may be controlled by the control unit.

Specifically, for example, a pulsed synchronizing signal (hereinafter referred to as external synchronizing signal sout for discrimination from the above internal synchronizing signal sin) is transmitted to the radiation image capturing apparatus from the control unit. The internal synchronizing signal sin is not emitted in the radiation image capturing apparatus, and the readout process RO of the image data D is performed synchronized with the external synchronizing signal sout transmitted from the control unit. The irradiating request signal sre is transmitted from the control unit to the generator of the radiation irradiating apparatus, and the generator may emit the radiation from the radiation irradiating apparatus according to the above transmitted irradiating request signal sre.

According to the above configuration, the control unit controls the synchronization and therefore the cycle $\tau$out of the external synchronizing signal sout and the cycle $\tau$re of the irradiating request signal sre transmitted by the control unit can be matched to be a predetermined cycle $\tau^*$ (see FIG. 14) throughout the moving image capturing. Therefore, if the control unit suitably shifts the timing of transmitting the irradiating request signal sre to the generator of the radiation irradiating apparatus at a predetermined time difference $\Delta\tau$ from the timing of transmitting the external synchronizing signal sout to the radiation image capturing apparatus, then the shift between the transmitting timing of the signals sout and sre at the predetermined time difference $\Delta\tau$ is maintained.

Therefore, as described above, it is possible to prevent the problem of the time interval T between the internal synchronizing signal sout and the irradiating request signal sre gradually shifting from the predetermined time difference $\Delta\tau$ while the moving image capturing progresses, and the radiation being irradiated from the radiation irradiating apparatus while the readout process RO of the image data D is being performed in the radiation image capturing apparatus.

However, according to the above configuration, the following problems may occur. That is, a plurality of frame images are captured in the moving image capturing, but the temperature of the readout IC, etc. of the radiation image capturing apparatus may increase, and the influence of the temperature on the readout image data D may change for each frame image. Therefore, the image quality of the frame images may change over time. When the influence of the change in temperature can be seen in the frame images, the moving image may be difficult to view when the moving image is played.

For example, in order to maintain the internal temperature of the radiation image capturing apparatus during capturing at a certain temperature, a process of warmup reset of the radiation detecting element may be performed to raise the temperature of the readout IC before capturing (different from the normal reset process of the radiation detecting element, the reset process of the radiation detecting element is performed while the readout IC is conducted, and the functional units such as the readout IC is warmed up).

In order to perform preprocess such as warmup reset in the radiation image capturing apparatus, a synchronizing signal is necessary. According to the above configuration, the radiation image capturing apparatus needs to be connected to the control unit to transmit the external synchronizing signal from the control unit to the radiation image capturing apparatus from the preprocess.

That is, before the moving image capturing is performed, the operator such as the radiation technician needs to turn on the power of the radiation image capturing apparatus and also needs to connect the radiation image capturing apparatus and the control unit in advance with a cable. Normally, the operator is used to the conventional operation in which the radiation image capturing apparatus automatically performs the preprocess once the power of the radiation image capturing apparatus is turned on. Therefore, if the operation of connecting the radiation image capturing apparatus to the cable is added in addition to turning on the power of the radiation image capturing apparatus when the moving image capturing is performed, the operator may consider the process to be troublesome and feel that the operability is difficult.

If the operator forgets to connect the cable to the radiation image capturing apparatus before capturing and the cable is connected to the radiation image capturing apparatus when the irradiation of radiation from the radiation irradiating apparatus is about to start for moving image capturing, the preprocess in the radiation image capturing apparatus starts from this point. Therefore, the operator may have to wait for the preprocess to end in the radiation image capturing apparatus and the radiation image capturing apparatus to be ready for capturing before the operator starts capturing.

In order to solve the above problem, the configuration as described below is possible. That is, according to the conventional process, the radiation image capturing apparatus automatically generates the internal synchronizing signal sin and starts the preprocess such as warmup reset when the power is turned on. When the operator connects the cable to the radiation image capturing apparatus and the external synchronizing signal sout is transmitted from the control unit, the radiation image capturing apparatus stops emitting the internal synchronizing signal and switches the control mode to operate according to the external synchronizing signal sout.

The control mode in which the radiation image capturing apparatus operates according to the internal synchronizing signal sin is called the internal synchronizing mode. The control mode in which the radiation image capturing apparatus operates according to the external synchronizing signal sout transmitted from the control unit is called the external synchronizing mode.

However, according to the above configuration, the internal synchronizing signal sin emitted by the radiation image capturing apparatus and the external synchronizing signal sout transmitted from the control unit cannot be synchronized. Therefore, normally, when the control mode switches from the internal synchronizing mode to the external synchronizing mode, the cycle of the readout process RO of the image data D in the radiation image capturing apparatus becomes a cycle τ different from the cycle τin of the internal synchronizing signal right before switching of the modes (or the cycle τout of the external synchronizing signal sout after switching).

That is, as shown in FIG. 15A, FIG. 15B, the time interval τ between the internal synchronizing signal sin right before switching the control mode and the external synchronizing signal sout right after switching the control mode may be longer (see FIG. 15A) or shorter (see FIG. 15B) than the cycle τin of the internal synchronizing signal sin (or the cycle τout of the external synchronizing signal sout after switching).

In FIG. 15A and FIG. 15B, the illustration of the irradiating request signal sre from the control unit to the generator of the radiation irradiating apparatus is omitted. Further, in FIG. 15A, when the external synchronizing signal sout (see external synchronizing signal shown with broken lines in the drawing) is received during the readout process RO of the image data D, the readout process RO performed at this point is continued, and control to synchronize is executed from the next external synchronizing signal sout that is transmitted.

As described above, in the radiation image capturing apparatus, the readout process RO of the image data D is performed for each frame with the internal synchronizing signal sin and the external synchronizing signal sout as the trigger. Therefore, if the readout process is performed in the cycle τin of the internal synchronizing signal sin (internal synchronizing mode, see FIG. 14), continuing time of the charge accumulating state I during the readout process of the image data D for each frame is a certain amount of time. If the time interval τ between the internal synchronizing signal sin right before switching the control mode and the external synchronizing signal sout right after switching is longer or shorter than the cycle τin of the internal synchronizing signal sin, the continuing time of the charge accumulating state I at the point that the control mode is switched becomes longer (see charge accumulating state I shown with A in FIG. 15A) or shorter (see charge accumulating state I shown with B in FIG. 15B) than the continuing time which is a certain amount of time.

Then, later on, the control mode becomes the external synchronizing mode, and the external synchronizing signal sout is transmitted from the control unit to the radiation image capturing apparatus at the same certain cycle τout. Therefore, the continuing time of the charge accumulating state I returns to a certain stable state. However, as described above, if the continuing time of the charge accumulating state I (see A in FIG. 15A or B in FIG. 15B) becomes longer or shorter and is disturbed when the control mode is switched, a few frames or few tens of frames may be used until the influence clears.

Therefore, even with such configuration, the operator cannot start moving image capturing until a certain amount of time passes (that is, time for a few frames or few tens of frames) after the radiation image capturing apparatus is connected to the control unit (that is, after the control mode is switched). Therefore, according to the above configuration, the operator needs to wait for the radiation image capturing apparatus to become a stable state in which capturing can be performed before the operator can start capturing, and may consider the operability to be poor.

SUMMARY

The present invention is conceived in view of the above problems, and an object of the present invention is to provide a radiation image capturing system which performs moving image capturing using a radiation image capturing apparatus configured to be able to start moving image capturing immediately after switching a control mode of the radiation image capturing apparatus from an internal synchronizing mode to an external synchronizing mode.

To achieve at least one of the abovementioned objects, according to an aspect of the present invention, a radiation image capturing system reflecting one aspect of the present invention is described, the radiation image capturing system which performs moving image capturing by irradiating a subject with radiation a plurality of times, the radiation image capturing system comprising: a radiation image capturing apparatus which performs a readout process of image data from a plurality of radiation detecting elements aligned two-dimensionally, a radiation irradiating apparatus which irradiates the radiation image capturing apparatus through a subject with radiation from a radiation source according to control by a generator; and a control device which transmits an external synchronizing signal to the radiation image capturing apparatus, which transmits an irradiating request signal to the generator of the radiation irradiating apparatus, and which synchronizes the radiation image capturing apparatus with the radiation irradiating apparatus, wherein, the radiation image capturing apparatus switches between control modes, the control modes being an internal synchronizing mode which performs a process according to an internal synchronizing signal emitted in the apparatus and an external synchronizing mode which performs a process with reference to the external synchronizing signal transmitted from the control device; when the external synchronizing signal transmitted from the control device is received, the radiation image capturing apparatus switches the control mode from the internal synchronizing mode to the external synchronizing mode; after the control mode is switched, the radiation image capturing apparatus starts the readout process of the image data at a timing delayed a predetermined amount of time from a timing that the external synchronizing signal is received; and the control device transmits the irradiating request signal to the generator of the radiation irradiating apparatus at a timing delayed a predetermined amount of time from a timing that the irradiating request signal should be transmitted to the generator.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 14 is a timing chart showing a relation among the internal synchronizing signal and the cycle in the radiation image capturing apparatus, the irradiating signal emitted by the generator of the radiation irradiating apparatus and the cycle, the transmitting timing, and the like.

FIG. 15A is a timing chart which describes the continuing time of the charge accumulating state becomes long at the point that the control mode is switched.

FIG. 15B is a timing chart which describes the continuing time of the charge accumulating state becomes short at the point that the control mode is switched.

DETAILED DESCRIPTION OF EMBODIMENTS

Hereinafter, one or more embodiments of the radiation image capturing apparatus according to the present invention will be described with reference to the drawings. However, the scope of the invention is not limited to the disclosed embodiments.

[Regarding Radiation Image Capturing Apparatus]

Figure 3:
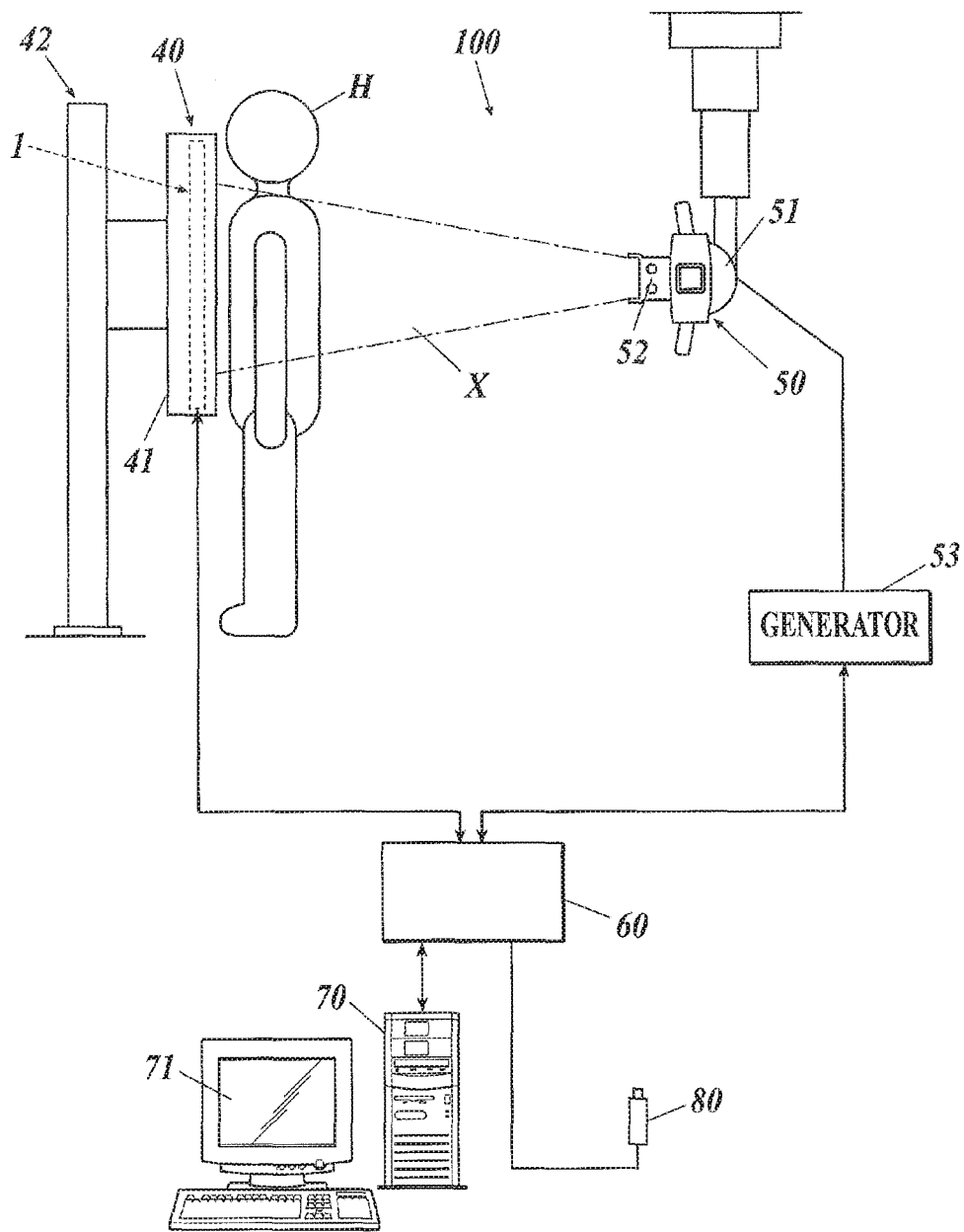
FIG. 3 is a diagram showing a configuration of a radiation image capturing system according to the present embodiment.

First, a configuration of the radiation image capturing apparatus used in the radiation image capturing system according to the present embodiment is described simply. As shown in FIG. 3 described below, an example in which a radiation image capturing apparatus 1 is portable (cassette type) is described. For example, the dedicated radiation image capturing apparatus may include the radiation image capturing apparatus 1 and a cassette holder of a capturing stage (see reference number 41 of FIG. 3) formed as one.

Figure 1:
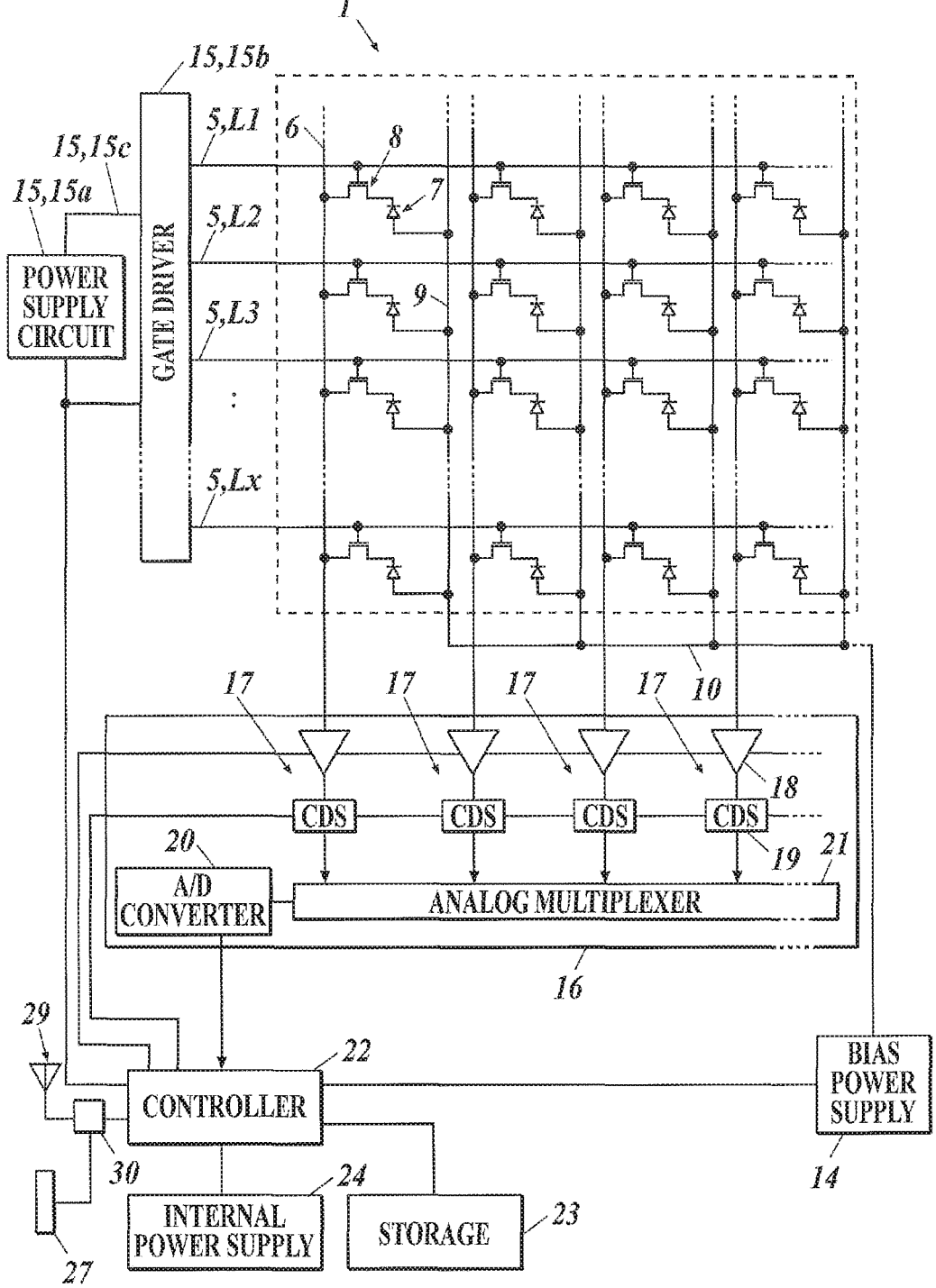
FIG. 1 is a block diagram showing an equivalent circuit of a radiation image capturing apparatus.

FIG. 1 is a block diagram showing an equivalent circuit of a radiation image capturing apparatus. As shown in FIG. 1, according to the radiation image capturing apparatus 1, a plurality of radiation detecting elements 7 are arranged in a two-dimensional array (matrix shape) and a rectangular array on a sensor substrate (not shown). Below, the radiation detecting element 7 may also be called a pixel. When radiation which passes a subject (not shown) is irradiated on the radiation detecting elements 7, charge is generated according to the amount of radiation. A reverse bias voltage is applied to the radiation detecting elements 7 from a bias power supply 14 through a bias line 9 or a connecting line 10.

A scanning driver 15 operates so that on voltage and off voltage supplied from a power supply circuit 15a through a line 15c are switched at a gate driver 15b and the voltage is applied to lines L1 to Lx included in scanning lines 5. A thin film transistor (TFT) 8 is connected to the radiation detecting elements 7 as a switch element. The TFT 8 turns off when an off voltage is applied through the scanning line 5. Conduction between the radiation detecting element 7 and a signal line 6 is cut and the charge generated in the radiation detecting element 7 is accumulated in the radiation detecting element 7. The TFT 8 turns on when the on voltage is applied through the scanning line 5. The charge accumulated in the radiation detecting element 7 is discharged to the signal line 6.

A plurality of readout circuits 17 are provided in a readout IC 16 and signal lines 6 are each connected to the readout circuit 17. When the TFTs 8 connected to the scanning line 5 on which the on voltage from the gate driver 15b is applied is turned on in a readout process RO of image data D from the radiation detecting elements, the charge from the radiation detecting element 7 is discharged through the TFT 8 to the signal line 6 and flows to the readout circuit 17. A voltage value output according to the flown amount of charge is output in an amplifying circuit 18 of the readout circuit 17.

The correlated double sampling circuit (described as "CDS" in FIG. 1) 19 reads out the voltage value output from the amplifying circuit 18 as the image data D with the analog value and outputs the above to the downstream side. The output image data D is sequentially transmitted to an A/D converter 20 through the analog multiplexer 21. The image data D with the digital value is sequentially converted with the A/D converter 20 and is sequentially stored in a storage 23. The on voltage is sequentially applied from the gate driver 15b to the lines L1 to Lx of the scanning line 5 so that the image data D is read out from the radiation detecting elements 7.

The controller 22 is composed of a computer including a central processing unit (CPU), a read only memory (ROM), a random access memory (RAM), an input/output interface, etc. connected to a bus, a field programmable gate array (FPGA), and the like (all are not shown). This can be composed from a dedicated control circuit.

A storage 23 including a static RAM (SRAM), a synchronous DRAM (SDRAM), a NAND flash memory is connected to the controller 22. A communicator 30 which communicates wirelessly or wired with an external device through an antenna 29 or connector 27 is connected to the controller 22. The above-described scanning driver 15, readout circuit 17, storage 23, bias power supply 14, and the like are connected to the controller 22. FIG. 1 shows the radiation image capturing apparatus 1 including an internal power supply 24, but alternatively, it is possible to receive supply of power from external devices.

[Process in Radiation Image Capturing Apparatus]

According to the present embodiment, when the moving image is captured, the radiation image capturing apparatus 1 alternately performs the above-described advancing to the charge accumulating state I and the readout process RO of the image data D.

Figure 2:
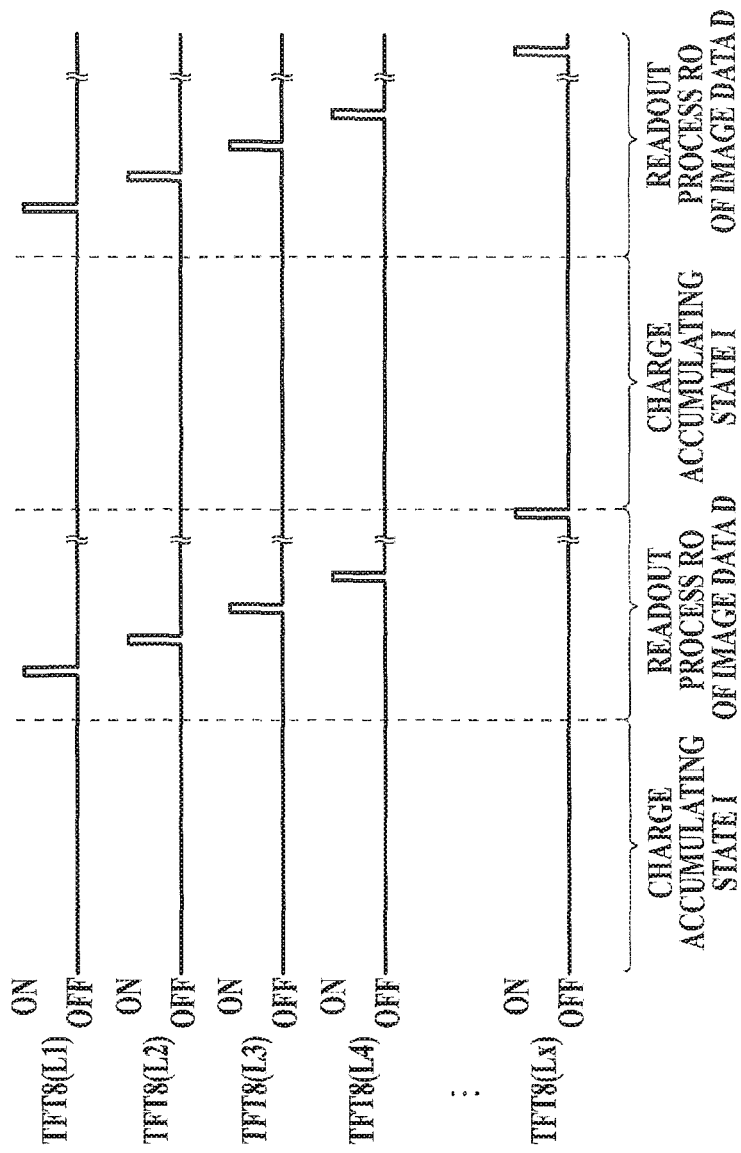
FIG. 2 is a timing chart showing timing to apply on voltage to scanning lines when the radiation image capturing apparatus advances to the charge accumulating state and performs the readout process of the image data.

Specifically, as shown in FIG. 2, the radiation image capturing apparatus 1 applies off voltage to the lines L1 to Lx of the scanning line 5 from the gate driver 15*b* of the scanning driver 15, turns off all TFTs 8, advances to the charge accumulating state I in which the radiation detecting elements 7 accumulate charge, and continues the charge accumulating state I for a predetermined amount of time (accumulating time). As described above, the radiation is irradiated from the radiation irradiating apparatus while the radiation image capturing apparatus 1 is in this charge accumulating state I.

On voltage is sequentially applied to the lines L1 to Lx of the scanning line 5 from the gate driver 15 and the TFTs 8 are sequentially turned on. The readout process RO of the image data D from the radiation detecting elements 7 is performed as described above and the image data D of one frame is read out (that is, image data D corresponding to one frame image). Then, the radiation image capturing apparatus 1 turns off all of the TFTs 8 and advances to the charge accumulating state I again.

Figure 14:
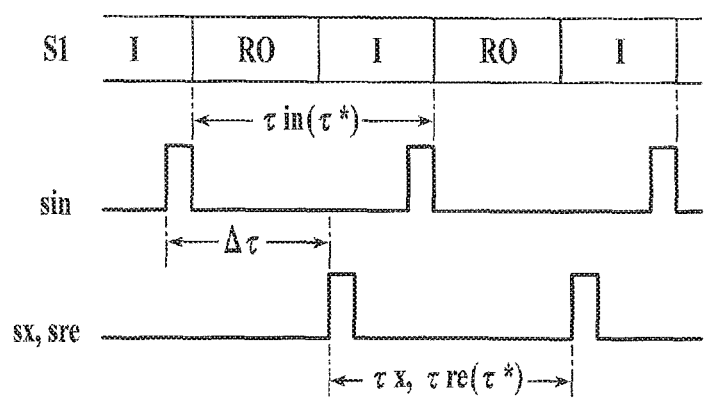

As described above, the radiation image capturing apparatus 1 repeats the following process alternately, advancing to the charge accumulating state I and the readout process RO of the image data D. As described above, the radiation image capturing apparatus 1 starts the process such as the readout process RO of the image data D according to the internal synchronizing signal sin (that is, synchronizing with the falling of the internal synchronizing signal sin as shown in FIG. 14). This point is described below together with switching the control mode.

[Regarding Radiation Image Capturing System]

Next, a radiation image capturing system 100 according to the present embodiment is described. The moving image capturing such as movement capturing performed with the subject standing is described, but the description is similar for moving image capturing with the subject laid down, and the present invention is applied to moving image capturing performed with the subject laid down. As shown in FIG. 3, the radiation image capturing system 100 includes a radiation image capturing apparatus 1, a radiation irradiating apparatus 50, a control unit 60, and an image processing apparatus 70.

The radiation image capturing apparatus 1 is loaded in a cassette holder 41 of a capturing stage 40, and the cassette holder 41 can be moved in a vertical direction along a supporting column 42 for positioning in the vertical direction. The apparatus can be a dedicated type (also called a provided type or fixed type) in which the radiation image capturing apparatus 1 and the cassette holder 41 are formed as one.

The radiation irradiating apparatus 50 includes a radiation source 51 including a rotating anode (not shown), a colli-mator 52 which performs the process such as focusing the irradiating field for the radiation X irradiated from the radiation source 51, and a generator 53 which irradiates the radiation X from the radiation source 51 and adjusts the amount of the radiation X. When tubular voltage, tubular electric current, irradiating time (or mAs value) is set in the generator 53, the generator 53 controls the irradiating of the radiation X from the radiation source 51 by irradiating the radiation X from the radiation source 51 in the amount (that is, percentage of amount and irradiating time) according to the above.

The generator 53 of the radiation irradiating apparatus 50 controls the radiation image capturing apparatus 1 to irradiate radiation X through the subject from the radiation source 51 according to the irradiating request signal sre each time the irradiating request signal sre is transmitted from the later described control unit 60. Details are described later. The setting of the tubular voltage on the generator 53 can be performed by operation on a computer other than the later described image processor 70.

The image processing apparatus 70 is a computer including a display 71 such as a cathode ray tube (CRT), a liquid crystal display (LCD), or the like. Alternatively, the image processing apparatus 70 can be a dedicated apparatus. As described below, when image data D, later described offset data O, later described true image data D* (see later described formula (2)) are transferred from the radiation image capturing apparatus 1, the image processing apparatus 70 generates frame images composing the captured moving image based on the above data and displays the moving image on the display 71

According to the present embodiment, further image correction can be performed on the generated frame images using the image processing apparatus 70. According to the present embodiment, the image processing apparatus 70 functions as a console to control the moving image capturing by transmitting a signal to the radiation image capturing apparatus 1, the generator 53 of the radiation irradiating apparatus 50, and the control unit 60 according to the operation by the operator such as the radiation technician. In the description below, the image processing apparatus 70 is described as console 70 when the device functions as the console. The image processing apparatus 70 can be configured as an apparatus separate from the console.

The control unit 60 is a dedicated device according to the present embodiment but alternatively may be a general computer. According to the present embodiment, the control unit 60 transmits the external synchronizing signal sout to the radiation image capturing apparatus 1 and transmits the irradiating request signal sre to the generator 53 of the radiation irradiating apparatus 50 so that the radiation image capturing apparatus 1 is controlled synchronized with the radiation irradiating apparatus 50. This point will be described in detail later.

The radiation image capturing system 100 according to the present embodiment is provided with an exposure switch 80 which is operated by the operator to start moving image capturing. The exposure switch 80 is provided outside a capturing chamber (for example, a front room) together with the image processing apparatus (console) 70 so that the operator is not exposed to radiation. An exposure switch provided in the radiation irradiating apparatus 50 can be used as the exposure switch 80, or as shown in FIG. 3, the exposure switch 80 can be attached to the control unit 60.

Figure 4A:
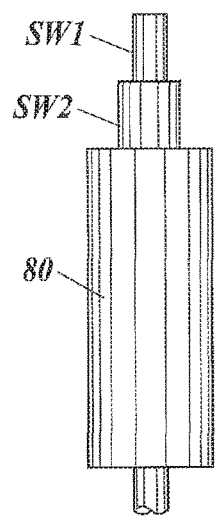
FIG. 4A is a diagram showing an example of an exposure switch.
Figure 4B:
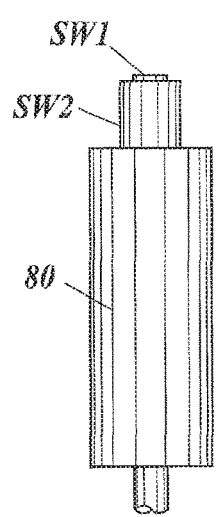
FIG. 4B is a diagram showing an example of an exposure switch half pressed.
Figure 4C:
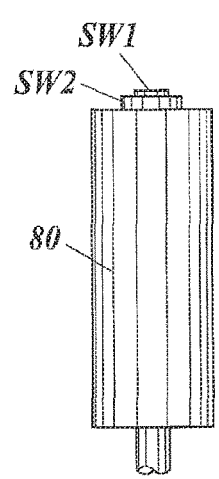
FIG. 4C is a diagram showing an example of an exposure switch fully pressed.

According to the present embodiment, the radiation irradiating apparatus 50 has a configuration as shown in FIG. 4A. The operator presses a first switch SW1 as shown in FIG. 4B (called half press, hereinafter referred to as SW1 operation), and then presses a second switch SW2 together with the first switch SW1 as shown in FIG. 4C (called full press, hereinafter referred to as SW2 operation).

The exposure switch 80 does not always need to be operated with 2 steps. Therefore, although in the description below, the exposure switch 80 is operated with 2 steps, any type can be applied with the SW1 operation showing the timing that the radiation source 51 is started by rotating the rotating anode of the radiation source 51 in the radiation irradiating apparatus 50 and the SW2 operation shows the timing as a trigger to start transmitting the irradiating request signal sre to the generator 53 of the radiation irradiating apparatus 50 to the control unit 60 as described later.

[Specific Process in Radiation Image Capturing System]

The specific process in the radiation image capturing system 100 according to the present embodiment is described.

[Pre-Process Before Starting Moving Image Capturing]

According to the present embodiment, the operator directly operates the generator 53 of the radiation irradiating apparatus 50 or operates the console 70 to set the tubular voltage, tubular electric current, irradiating time (or mAs value), etc. for the generator 53. When the operator turns on the power of the radiation image capturing apparatus 1 used in the moving image capturing, the radiation image capturing apparatus 1 performs the predetermined initial operation and the controller 22 of the radiation image capturing apparatus 1 (see FIG. 1) starts emitting the pulsed internal synchronizing signal sin in a predetermined cycle τin to predetermined functional units such as the scanning driver 15, the readout IC 16, etc. The radiation image capturing apparatus 1 is able to start emitting the internal synchronizing signal sin at the point when the capturing start signal is transmitted from the console 70 according to operation from the operator.

According to the present embodiment, the control mode of the radiation image capturing apparatus 1 right after turning on the power is set to an internal synchronizing mode which performs the process according to the internal synchronizing signal sin emitted in the apparatus. As described later, the external control signal sout is transmitted from the control unit 60 to the radiation image capturing apparatus 1, but at this point, the external control signal sout is not yet transmitted from the control unit 60. The internal synchronizing signal sin emitted in the radiation image capturing apparatus 1 and the external synchronizing signal sout emitted from the control unit 60 are set in advance so that the cycles τin, τout are to be the same cycle.

According to the radiation image capturing apparatus 1, when the internal synchronizing signal sin is emitted from the controller 22, the warmup reset of the radiation detecting element 7 is started according to the signal (that is, synchronized with the falling of the internal synchronizing signal sin). That is, according to the present embodiment, when the power of the radiation image capturing apparatus 1 is turned on, pre-process such as the warmup reset is performed automatically. That is, according to the present embodiment, the operator only needs to turn on the power (or additionally transmit the capturing start signal from the console 70) to perform the pre-process in the radiation image capturing apparatus 1 and does not need to perform other operation such as connect the radiation image capturing apparatus 1 with the control unit 60.

As described above, the warmup preset is a pre-process to raise the temperature of the readout IC 16 in advance before capturing, and unlike the normal reset process of the radiation detecting element 7, the reset process of the radiation detecting element 7 is performed with the readout IC 16 also in the conducted state.

Figure 5:
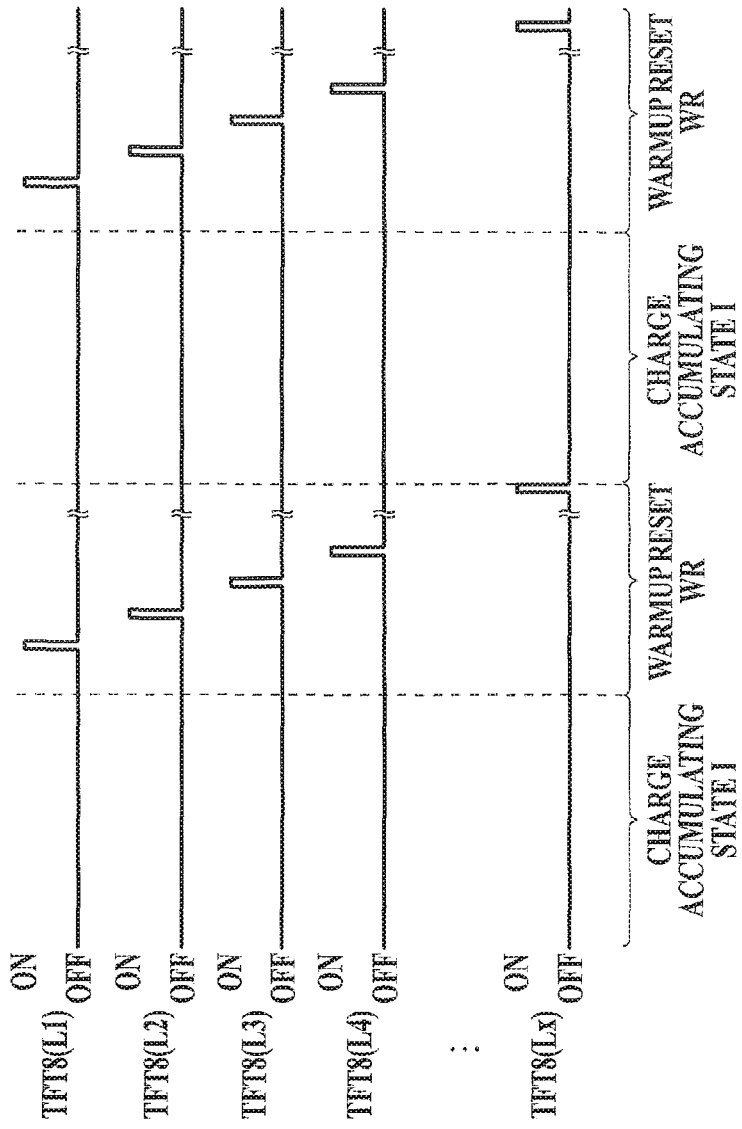
FIG. 5 is a timing chart showing timing of applying on voltage to scanning lines when a warmup reset of a radiation detecting element is performed before capturing.

In this case, as shown in FIG. 5, the radiation image capturing apparatus 1 performs the warmup reset WR of the radiation detecting element 7 in the same processing sequence as the readout process RO of the image data D when the moving image capturing is performed as described in FIG. 2. That is, at the same timing as the readout process RO of the image data D, the on voltage is sequentially applied to the lines L1 to Lx of the scanning line 5 from the gate driver 15b of the scanning driver 15, and the warmup reset WR of the radiation detecting element 7 is performed. Although the readout IC 16 is conducted when the warmup reset WR is performed, the readout IC 16 does not perform the readout operation.

According to the present embodiment, as described above, the internal synchronizing signal sin and the external synchronizing signal sout are emitted at the same cycle, and the warmup reset WR (see FIG. 5) of the radiation detecting element 7 is performed in the same process sequence as the readout process RO (see FIG. 2) of the image data D. Therefore, similar to the readout process RO of the image data D shown in FIG. 2, when the warmup reset WR ends, the state advances to the charge accumulating state I (see FIG. 5) when the warmup reset WR of the radiation detecting element 7 is performed before starting the moving image capturing. The continuing time of the charge accumulating state I (see FIG. 5) before starting the moving image capturing is the same time as the continuing time of the charge accumulating state I (see FIG. 2) when the readout process RO of the image data D is performed after starting the moving image capturing.

The system can be configured so that when the warmup reset WR of the radiation detecting element 7 is performed as described above in the radiation image capturing apparatus 1 and the temperature in the radiation image capturing apparatus 1 reaches a predetermined temperature, a signal is emitted from the radiation image capturing apparatus 1 to the console 70, and a notice is displayed on the display 71 of the console 70 to notify to the operator that the moving image capturing can be performed.

[Regarding Process when Switching Control Modes in Radiation Image Capturing Apparatus]

Next, when the operator performs SW1 operation (half press, see FIG. 4B) on the exposure switch 80 to start the moving image capturing, the generator 53 of the radiation irradiating apparatus 50 starts rotating the rotating anode and starts the radiation source 51.

According to the present embodiment, when the SW1 operation is performed on the exposure switch 80, this acts as a trigger (to be accurate, an unlock signal transmitted from the radiation image capturing apparatus 1 as described later acts as a trigger) to start transmitting of an external synchronizing signal sout (cycle τout) from the control unit 60 to the radiation image capturing apparatus 1. At this point, the control unit 60 does not yet transmit the irradiating request signal sre to the generator 53 of the radiation irradiating apparatus 50, and the irradiating of radiation from the radiation source 51 does not start.

When the external synchronizing signal sout transmitted from the control unit 60 is received, the radiation image capturing apparatus 1 switches the control mode from the internal synchronizing mode to the external synchronizing mode (that is, the mode which performs the readout process RO of the image data D on the basis of the external synchronizing signal sout transmitted from the control unit 60).

As described above, the cycles τin, τout of the internal synchronizing signal sin transmitted in the radiation image capturing apparatus 1 and the external synchronizing signal sout transmitted from the control unit 60 are the same, but the cycles are not synchronized. Therefore, similar to conventional examples (see FIG. 15A, FIG. 15B), when the control mode of the radiation image capturing apparatus 1 is switched from the internal synchronizing mode which performs the process such as the warmup reset WR of the radiation detecting element 7 according to the internal synchronizing signal sin to the mode which simply performs the readout process RO of the image data D according to the external synchronizing signal sout, the continuing time of the charge accumulating state I at the point when the control mode is switched may be longer (see FIG. 15A) or shorter (see FIG. 15B) than the continuing time up to this point.

Therefore, this causes the previously described problem that the operator needs to wait a few frames or a few tens of frames until the influence of the continuing time of the charge accumulating state I becoming longer or shorter clears before the operator can start capturing.

According to the present embodiment, in order to prevent such problems, the radiation image capturing apparatus 1 switches the control mode to the external synchronizing mode when the external synchronizing signal sout is transmitted from the control unit 60. After the control mode is switched, the process such as the readout process RO of the image data D starts at the timing delayed for a predetermined amount of time from the timing that the external synchronizing signal sout is received and not at the timing that the external synchronizing signal sout is received (that is, not synchronized with the external synchronizing signal sout).

Therefore, according to the present embodiment, the internal synchronizing mode is a conventional mode which performs the process according to the internal synchronizing signal sin (that is, synchronized with the internal synchronizing signal sin) emitted with the apparatus, whereas the external synchronizing mode is not a mode which performs the readout process RO of the image data according to the external synchronizing signal sout (that is, synchronized with the external synchronizing signal sout) transmitted from the control unit 60 but is a mode which performs the readout process RO of the image data D on the basis of the external synchronizing signal sout transmitted from the control unit 60 (that is, a mode which performs the process of the readout process RO of the image data D synchronized with the timing delayed a predetermined amount of time from the external synchronizing signal sout).

The specific description is provided below. As described above, the internal synchronizing signal sin emitted in the radiation image capturing apparatus 1 and the external synchronizing signal sout emitted from the control unit 60 are not synchronized in the present embodiment. Therefore, the radiation image capturing apparatus 1 performs the process such as the readout process RO of the image data D according to the external synchronizing signal sout as described in FIG. 15A and FIG. 15B.

Figure 6:
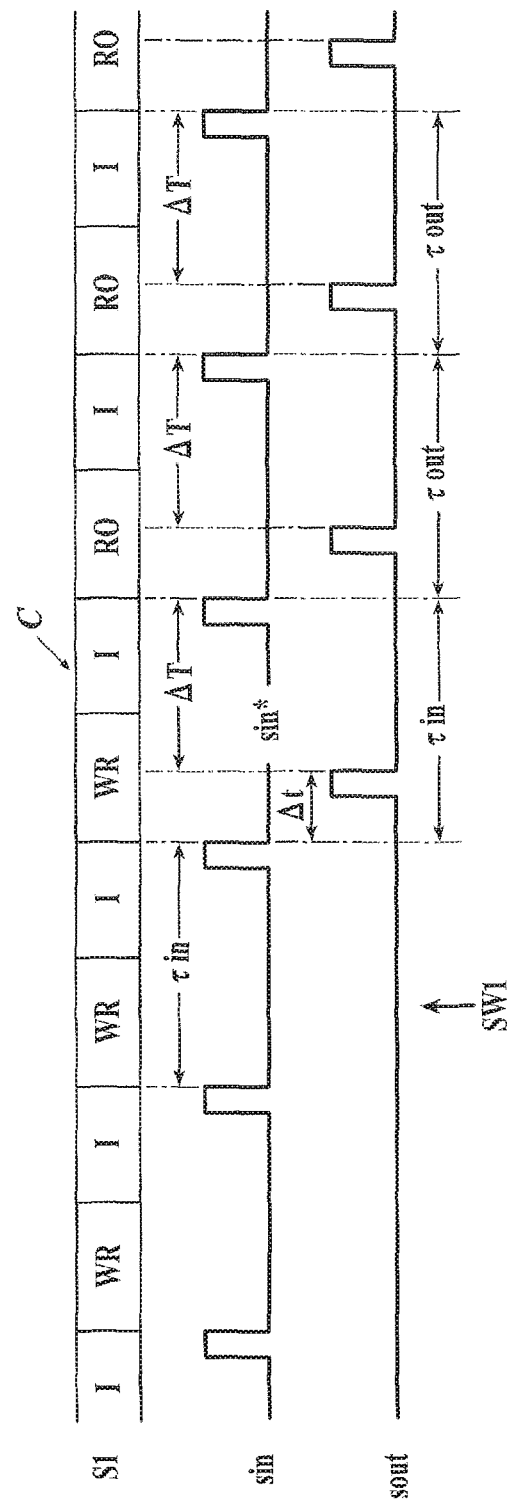
FIG. 6 is a timing chart showing timing that internal synchronizing signals, external synchronizing signals, and new synchronizing signals are emitted before and after control modes of the radiation image capturing apparatus of the present embodiment are switched.

According to the present embodiment, when the control mode is switched from the internal synchronizing mode to the external synchronizing mode, the controller 22 of the radiation image capturing apparatus 1 stops emitting the internal synchronizing signal sin and as shown in FIG. 6, obtains the phase difference Δt between the internal synchronizing signal sin right before the control mode is switched and the external synchronizing signal sout right after the control mode is switched. The unit of the phase difference Δt is time (millisecond or μsecond). SW1 shown in FIG. 6 shows the timing that the SW1 operation is performed on the exposure switch 80.

The internal synchronizing signal sin may be continued to be emitted after switching the control mode, but in such case, after the control mode is switched, the process in the radiation image capturing apparatus 1 is performed on the basis of a new synchronizing signal sin* described later and not the internal synchronizing signal sin.

Then, according to the formula (1), the controller 22 of the radiation image capturing apparatus 1 subtracts the phase difference Δτ obtained as described above from the cycle τin of the internal synchronizing signal sin emitted up to this point and calculates a difference ΔT.

$$\Delta T = \tau in - \tau t \quad (1)$$

Then, the controller 22 of the radiation image capturing apparatus 1 sets this difference ΔT as the predetermined amount of time. After switching to the external synchronizing mode of the control mode, as shown in FIG. 6, each time the external synchronizing signal sout is received, a new synchronizing signal sin* is emitted so that the signal falls at a timing delayed for a predetermined amount of time, that is, in the amount of the above difference ΔT from the timing of the falling of the external synchronizing signal sout. Then, each functional unit such as the scanning driver 15 starts the process such as the readout process RO of the image data D at the timing that the new synchronizing signal sin* falls.

According to the present embodiment, after the control mode is switched to the external synchronizing mode, the functional units such as the scanning driver 15 perform the process according to the new synchronizing signal sin* emitted by the controller 22 instead of the received external synchronizing signal sout.

According to the above configuration, first, the time interval between the internal synchronizing signal sin right before the control mode is switched and the external synchronizing signal sout right after the control mode is switched at the point when the control mode is switched from the internal synchronizing mode to the external synchronizing mode in the radiation image capturing apparatus 1 is to be the same as the cycle τin of the internal synchronizing signal sin up to this point. Therefore, different from the conventional example shown in FIG. 15A, FIG. 15B, as shown in FIG. 6, according to the present embodiment, the continuing time of the charge accumulating state I (see C in drawing) at the point of switching the control mode is to be the same as the continuing time of the charge accumulating state I up to this point.

Therefore, according to the present embodiment, the problem of having to wait for a few frames to a few tens of frames until the influence of the continuing time of the charge accumulating state I being long or short is clear before starting the capturing does not occur. The operator is able to perform moving image capturing by performing the SW1 operation (half press) on the exposure switch 80 and then performing the SW2 operation (full press) one second after, similar to the normal operation. That is, the moving image capturing is performed by, after performing the SW1 operation, performing the SW2 operation right away (about one second later) without having to wait for the start of capturing.

After switching the control mode to the external synchronizing mode, the functional unit such as the scanning driving unit 15 starts the process such as the readout process RO of the image data O according to the new synchronizing signal sin* emitted by the controller 22 each time the radiation image capturing apparatus 1 receives the external synchronizing signal sout. Therefore, after switching the control mode, the readout process RO of the image data D starts at a timing delayed a predetermined amount of time (difference ΔT) from the timing that the external synchronizing signal sout is received.

Then, as described above, according to the present embodiment, the cycle τin of the internal synchronizing signal sin emitted in the radiation image capturing apparatus 1 is preset to be the same cycle as the cycle τout of the external synchronizing signal sout emitted from the control unit 60. Therefore, even after the control mode is switched, the continuing time of the charge accumulating state I stays the same and maintains a certain amount of time. Consequently, from this viewpoint also, the operator does not have to wait a few frames to a few tens of frames before starting the moving image capturing and the operator is able to perform the SW2 operation on the exposure switch 80 and start the moving image capturing right away.

As described above, in the radiation image capturing apparatus 1, the functional unit such as the scanning driver 15 starts the process according to the internal synchronizing signal sin before switching the control mode and starts the process according to the new synchronizing signal sin* delayed a predetermined amount of time (difference ΔT) from the external synchronizing signal after switching the control mode. Therefore, the process is performed at a certain cycle τin (cycle τout after switching) before and after switching the control mode.

[Regarding Setting of Time Difference between External Synchronizing Signal and Irradiating Request Signal in Control Unit]

After the above, when the operator performs the SW2 operation on the exposure switch 80, the control unit 60 starts the transmitting of the irradiating request signal sre to the generator 53 of the radiation irradiating apparatus 50 and repeatedly transmits the irradiating request signal sre at a predetermined cycle τre. Each time the irradiating request signal sre is received from the control unit 60, the generator 53 irradiates radiation from the radiation source 51.

Figure 7:
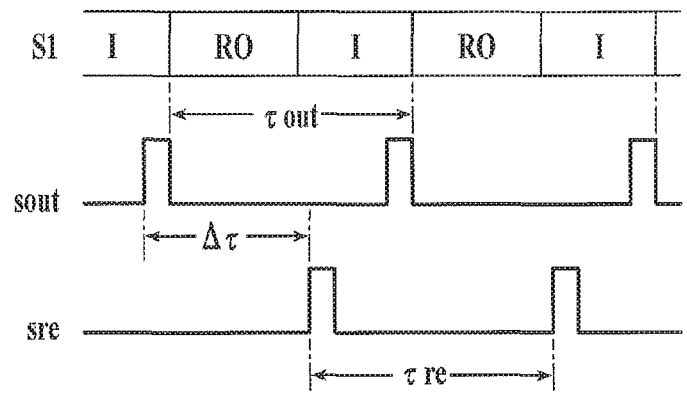
FIG. 7 is a timing chart showing timing that the external synchronizing signal and the irradiating request signal are transmitted from a control unit if the radiation image capturing apparatus operates according to an external synchronizing signal.

Then, according to the present embodiment, the control unit 60 adjusts the cycle τre of the irradiating request signal sre transmitted to the generator 53 of the radiation irradiating apparatus 50 to be the same cycle as the cycle τout of the external synchronizing signal sout transmitted to the radiation image capturing apparatus 1. Then, as shown in FIG. 7, if the radiation image capturing apparatus 1 operates according to the external synchronizing signal sout, the control unit 60 transmits the irradiating request signal sre to the generator 53 of the radiation irradiating apparatus 50 delayed for a predetermined time difference Δτ from the timing that the external synchronizing signal sout is transmitted to the radiation image capturing apparatus 1 so that the radiation image capturing apparatus 1 is irradiated with the radiation from the radiation irradiating apparatus 50 while in the charge accumulating state I (that is, so that the radiation is irradiated while the readout process RO of the image data D is performed).

However, according to the present embodiment, as described above (see FIG. 6), after the control mode is switched, the radiation image capturing apparatus 1 changes the control to perform the process according to the new synchronizing signal sin* delayed a predetermined amount of time (difference ΔT) from the external synchronizing signal sout instead of the external synchronizing signal sout transmitted from the control unit 60.

Therefore, the control unit 60 needs to transmit the irradiating request signal sre to the generator 53 of the radiation irradiating apparatus 50 delayed for a predetermined amount of time (difference ΔT) or there is a possibility that the radiation may be irradiated from the radiation irradiating apparatus 50 while the readout process RO of the image data D is performed in the radiation image capturing apparatus 1. However, the control unit 60 is not able to know the amount of time that is set as the predetermined amount of time (difference ΔT) in the radiation image capturing apparatus 1.

Therefore, according to the present embodiment, at the point when the control mode is switched to the external synchronizing mode, the controller 22 of the radiation image capturing apparatus 1 calculates the difference ΔT which is the predetermined amount of time according to the above formula (1) and transmits the information of the difference ΔT (that is, predetermined amount of time) calculated in the control unit 60.

Figure 8:
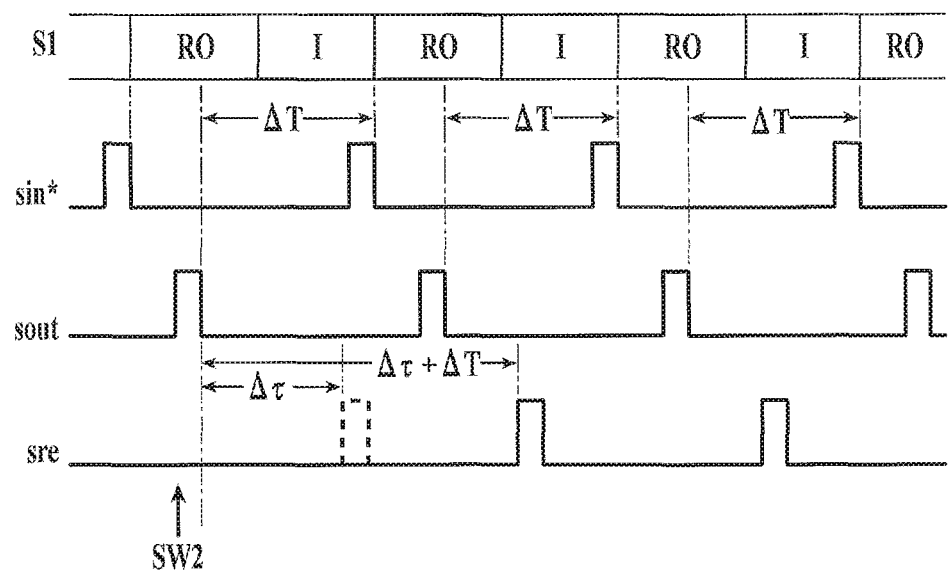
FIG. 8 is a timing chart showing a relation between the timing that the new synchronizing signal is emitted in the radiation image capturing apparatus and the timing that the external synchronizing signal and the irradiating request signal are emitted from the control unit according to the present embodiment.

Based on the SW2 operation performed later, when the irradiating request signal sre is transmitted to the generator 53 of the radiation irradiating apparatus 50, as shown in FIG. 8, the control unit 60 transmits the irradiating request signal sre to the generator 53 of the radiation irradiating apparatus 50 at the timing (that is, timing a time difference Δτ+ΔT from the external synchronizing signal sout) delayed a predetermined amount of time (that is, difference ΔT) than the timing that the irradiating signal sre should be transmitted (see irradiating request signal sre with broken lines in the drawing, that is, timing delayed for a normal time difference Δτ after transmitting the external synchronizing signal sout to the radiation image capturing apparatus 1 as shown in FIG. 7).

Figure 9:
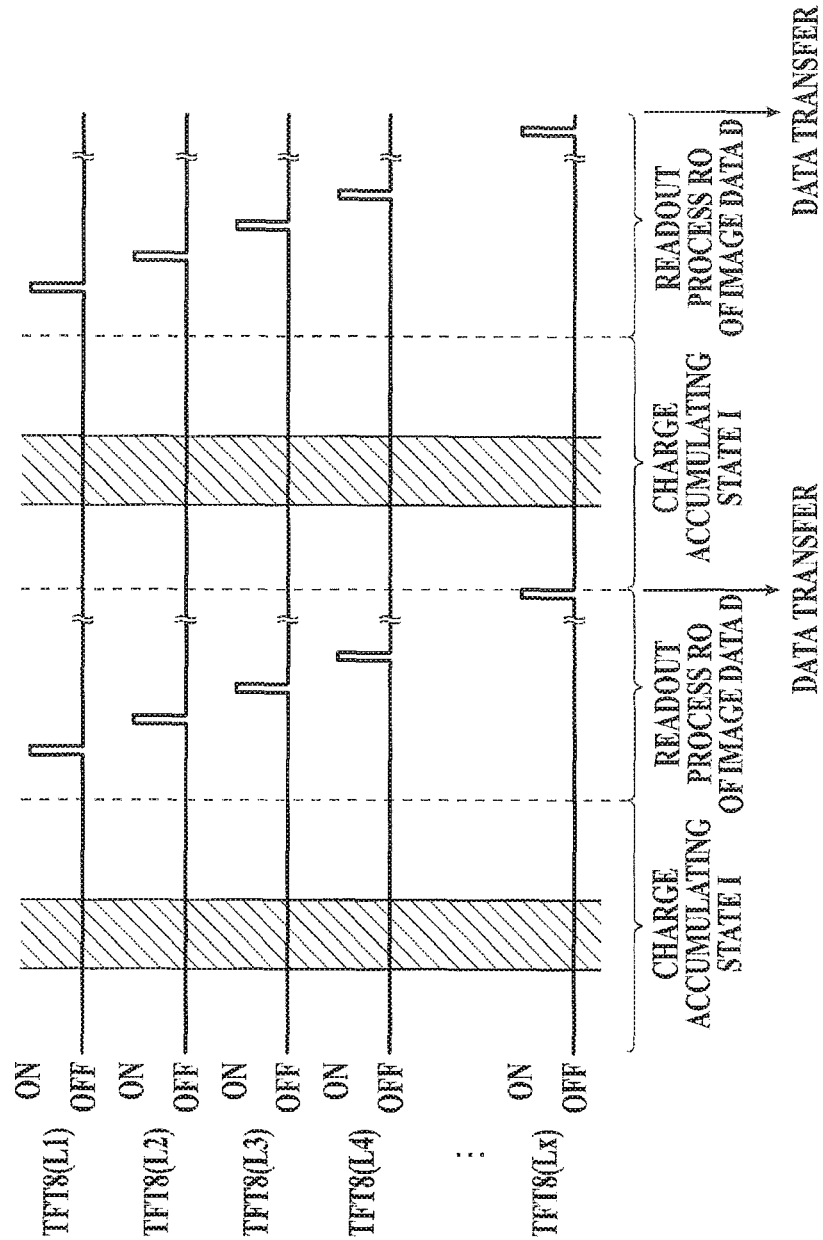
FIG. 9 is a timing chart showing radiation is surely irradiated from the radiation irradiating apparatus while the radiation image capturing apparatus is in the charge accumulating state according to the present embodiment.

According to the above-described configuration, as shown in FIG. 9, the radiation is irradiated from the radiation source 51 of the radiation irradiating apparatus 50 while the radiation image capturing apparatus 1 is in the charge accumulating state I. Therefore, it is possible to prevent the radiation from being irradiated while the readout process RO of the image data D is performed in the radiation image capturing apparatus 1, and it is possible to accurately perform the moving image capturing. The term that the radiation is irradiated is shown with diagonal lines in FIG. 9. The data transfer in the drawings is described later.

As described above, the process of transmitting the irradiating request signal sre from the control unit 60 to the generator 53 of the radiation irradiating apparatus 50 is started after the operator performs the SW2 operation on the exposure switch 80 (see SW2 in drawing) as shown in FIG. 8, and until then, the control unit 60 does not start transmitting the irradiating request signal sre to the generator 53. At the point that the transmitting of the external synchronizing signal sout to the radiation image capturing apparatus 1 is started (that is, the point that the control mode of the radiation image capturing apparatus 1 is switched), the control unit 60 performs the process of calculating and setting the new time difference Δτ+ΔT based on the predetermined amount of time, that is, the difference ΔT transmitted from the radiation image capturing apparatus 1.

[Readout Process of Offset Data in Radiation Image Capturing Apparatus]

According to the present embodiment, the radiation image capturing apparatus 1 performs the readout process RO of the image data D and reads out the offset data O in a state where the radiation is not irradiated from the radiation irradiating apparatus 50 after the operator performs the SW1 operation on the exposure switch 80 (that is, after the control mode of the radiation image capturing apparatus 1 switches to the external synchronizing mode) and before the SW2 operation is performed and the radiation starts to be irradiated from the radiation irradiating apparatus 50 (that is, after the control mode is switched as shown in FIG. 6, until the SW2 operation shown in FIG. 8 is performed).

Dark current (also called dark charge) is always occurring in the radiation detecting element 7 of the radiation image capturing apparatus 1 due to the thermal excitation by the heat (temperature) of the radiation detecting element 7 itself. The offset amount due to the dark current is superimposed to the image data D readout in the readout process RO of the image data D in the moving image capturing. According to the following formula (2), the offset data O from the readout image data D is subtracted for each radiation detecting element 7 so that true image data D* from only the charge generated in the radiation detecting element 7 by the irradiating of the radiation and not including the offset amount of the dark current can be calculated.

$$D^* = D - O \tag{2}$$

The offset amount due to the dark current, that is, the offset data O can be read out by performing the readout process in the same process sequence as the readout process RO of the image data D with the radiation not being irradiated to the radiation image capturing apparatus 1. After the control mode of the radiation image capturing apparatus 1 is switched to the external synchronizing mode, and before the SW2 operation is performed and the irradiating of the radiation from the radiation irradiating apparatus 50 starts, the readout process in the same process sequence as the readout process RO of the image data D in the later moving image capturing is performed with the radiation not being irradiated to the radiation image capturing apparatus 1 (see FIG. 6). Therefore, the data read out in this term can be used as the offset data O.

According to the above configuration, the offset data O can be readout automatically and accurately in the series of operations for performing the moving image capturing using the radiation image capturing apparatus 1. Therefore, there is no need for the operator to perform the operation or process to further readout the offset data O before or after the moving image capturing, and the ease of use of the radiation image capturing system 100 is enhanced for the operator.

The data read out in one readout process of a frame in the above term can be considered to be the offset data O. Alternatively, offset data o for each of a plurality of frames within the above term (hereinafter called offset data o in order to discriminate from the offset data O as the final value) may be readout, and an average value (any other statistics such as intermediate value, mode) of the offset data o for the plurality of frames can be calculated for each radiation detecting element 7 so as to obtain the offset data O for each radiation detecting element 7.

When the offset data O is calculated as an average value of the offset data o for a plurality of frames, for example, it is possible to calculate the average value of the offset data o readout in the readout process in the plurality of frames right after the control mode of the radiation image capturing apparatus 1 is switched to the external synchronizing mode when the operator performs the SW1 operation (half press) on the exposure switch 80.

The plurality of frames in which the offset data O is read out are shifted while the movement average of the offset data O is calculated, and this can be used as the offset data O.

Figure 10A:
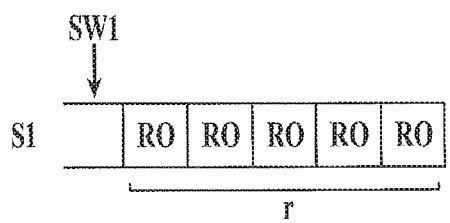
FIG. 10A, FIG. 10B, and FIG. 10C are diagrams describing that a moving average is calculated by shifting a range of a predetermined number of frames as the target when the offset data is calculated with the movement average.

Specifically, for example, as shown in FIG. 10A, after the operator performs the SW1 operation on the exposure switch 80 (see SW1 in the drawing), the average value of the offset data O readout in the readout process RO for the first predetermined number of frames is calculated and the average value is saved in the RAM as the offset data O.

Figure 10B:
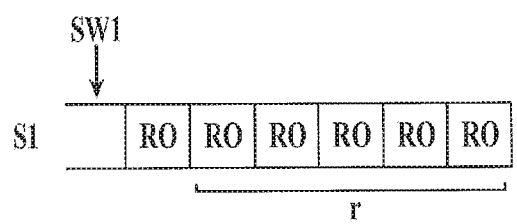

Then, as shown in FIG. 10B, when the operator does not perform the exposure switch SW2 operation and the next readout process RO is performed, the range r of the predetermined number of the plurality of frames as the target of calculating the offset data O is shifted so as to include the frames in which the present readout process RO is performed to calculate the average value (that is, movement average) of the offset data o and the average value is overwritten and updated in the RAM as the offset data O.

As described above, each time the readout process RO is performed without the SW2 operation being performed, the range r of the predetermined number of the plurality of frames as the target of calculating the offset data O is shifted and the movement average of the offset data o is calculated to update the offset data O. The description of the charge accumulating state I is omitted in FIG. 10A and FIG. 10B, and FIG. 10C described below. The example shows the number of frames as the target of calculating the movement average (that is, the frame of the above-described range r) is five frames, but the number of frames can be more than or less than five.

Figure 10C:
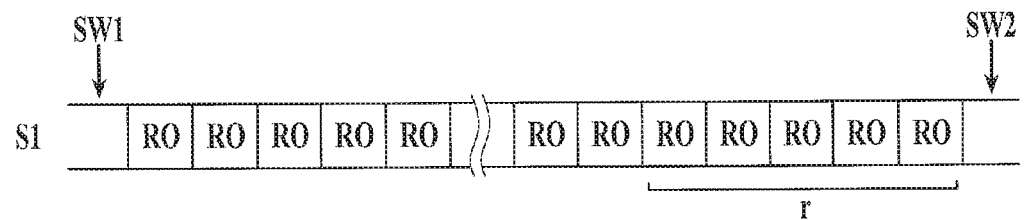

Then, as shown in FIG. 10C, when the operator performs the SW2 operation (full press), the offset data O calculated as the average value of the readout offset data o for a predetermined number of the plurality of frames including the readout process RO performed right before (that is, the offset data O which is last overwritten and updated in the RAM before the SW2 operation) can be used as the offset data O.

For example, when the amount of time until the SW2 operation (full press) is performed is long after the operator performs the SW1 operation (half press) on the exposure switch 80, instead of using the offset data O calculated based on the offset data o read out far before the start of moving image capturing, it is preferable to use the offset data O calculated based on the offset data o readout right before the start of the moving image capturing because the offset data O is obtained with the conditions close to the conditions of the moving image capturing that is performed. When the offset data O is calculated as the movement average, the offset data O can be calculated based on the offset data o readout right before starting the moving image capturing.

[Process When SW2 Operation of Exposure Switch is Performed]

Next, when the operator performs the SW2 operation on the exposure switch 80, the radiation is irradiated from the radiation source 51 of the radiation irradiating apparatus 50 to the radiation image capturing apparatus 1 through the subject a plurality of times to perform the moving image capturing.

When the operator performs the SW2 operation on the exposure switch 80, the control unit 60 transmits the irradiating start signal to the radiation image capturing apparatus 1. The radiation image capturing apparatus 1 advances to the charge accumulating state I at the point when the readout process RO being performed at the time ends, and transmits the unlock signal (also called interlock release signal) to the control unit 60.

The radiation image capturing apparatus 1 continues after transmitting the unlock signal to repeat the process of performing the readout process RO of the image data D with reference to the external synchronizing signal sout transmitted in the cycle τout from the control unit 60 (that is, synchronizing with the timing delayed for a difference ΔT from the external synchronizing signal sout) and advancing to the charge accumulating state I as shown in FIG. 6.

When the unlock signal is transmitted from the radiation image capturing apparatus 1, the control unit 60 starts transmitting the irradiating request signal sre to the generator 53 of the radiation irradiating apparatus 50 as shown in FIG. 8. That is, as described above (see FIG. 8), the irradiating request signal sre is transmitted to the generator 53 for each cycle τre (equal to cycle τout) so that the irradiating request signal sre is transmitted to the generator 53 of the radiation irradiating apparatus 50 at the timing delayed a predetermined amount of time (that is, difference ΔT) from the original timing that the irradiating request signal sre should be transmitted (see broken line in drawing showing the irradiating request signal sre).

Then, the generator 53 of the radiation irradiating apparatus 50 irradiates the radiation X to the radiation image capturing apparatus 1 through the subject from the radiation source 51 each time the irradiating request signal sre is transmitted from the control unit 60 (see FIG. 3). Therefore, as shown in FIG. 9, the radiation is accurately irradiated while the radiation image capturing apparatus 1 is in the charge accumulating state I.

[Regarding Data Transfer]

For example, the image data D readout for each frame in the radiation image capturing apparatus 1 is stored in the storage 23 (see FIG. 1) of the radiation image capturing apparatus 1. After the moving image capturing ends, the image data D can be transferred from the radiation image capturing apparatus 1 to the image processing apparatus 70 with the offset data O. In this case, in the image processing apparatus 70, according to the formula (2), the offset data O is subtracted from the image data D of each frame and the true image data D* is calculated for each radiation detecting element 7. The image process is performed on the calculated true image data D* to generate each frame image.

As shown in FIG. 9, each time the readout process RO of the image data D is performed in the radiation image capturing apparatus 1 (that is, for each frame), the image data D is able to transfer the image data D to the image processing apparatus 70. In this case, if the offset data O is transferred to the image processing apparatus 70 before the moving image capturing is started, when the image data D is transferred for each frame, the subtracting process according to the above formula (2) is performed immediately in the image processing apparatus 70 to calculate the true image data D*. The image process is performed on the calculated true image data D* and the frame images are generated in real time (that is, parallel to the moving image capturing) to be displayed on the display 71.

As described in FIG. 9, when the data is transferred to the image processing apparatus 70 each time the readout process RO of the image data D is performed in the radiation image capturing apparatus 1, instead of transferring the image data D as described above, the subtracting process is performed according to the above-described formula (2) in the radiation image capturing apparatus 1 to calculate the true image data D*. The calculated true image data D* can be transferred to the image processing apparatus 70.

According to the above configuration, the offset data O does not need to be transferred from the radiation image capturing apparatus 1 to the image processing apparatus 70. Since there is no need to perform the subtracting process according to the above formula (2) in the image processing apparatus 70, it is possible to generate the frame images faster, and the frame images can be displayed on the display 71 of the image processing apparatus 70 in real time.

[End of Moving Image Capturing]

According to the present embodiment, when the SW2 operation on the exposure switch 80 by the operator ends (specifically, when the operator releases the full press of the exposure switch 80), the generator 53 of the radiation irradiating apparatus 50 stops the irradiating of radiation from the radiation source 51, and with this, the moving image capturing ends.

For example, how the moving image capturing ends can be suitably determined. Examples include ending the moving image capturing when the radiation is irradiated a preset number of times (specified frame number) or ending the moving image capturing when the whole irradiating time set in advance passes.

[Effect]

As described above, according to the radiation image capturing system 100 of the present embodiment, the control unit 60 transmits the external synchronizing signal sout to the radiation image capturing apparatus 1 and transmits the irradiating request signal sre to the generator 53 of the radiation irradiating apparatus 50, and the control unit 60 controls the moving image capturing while controlling the synchronizing of the above.

Consequently, it is possible to prevent the following problems of the conventional system where the timing of the readout process RO of the image data D in the radiation image capturing apparatus 1 and the timing of irradiating the radiation from the radiation irradiating apparatus 50 gradually shifts while the moving image capturing is performed, and the radiation is irradiated while the readout process RO of the image data D is still performed in the radiation image capturing apparatus 1. With this, the moving image capturing can be accurately performed.

After switching the control mode of the radiation image capturing apparatus 1 from the internal synchronizing mode to the external synchronizing mode, the process in the radiation image capturing apparatus 1 is performed at the timing delayed a predetermined amount of time from the timing that the external synchronizing signal sout is received (that is, according to the new synchronizing signal sin* emitted delayed a predetermined amount of time (that is, the difference ΔT) from the external synchronizing signal sout), instead of according to the external synchronizing signal sout transmitted from the control unit 60.

Therefore, when the control mode in the radiation image capturing apparatus 1 is switched from the internal synchronizing mode to the external synchronizing mode, since the readout process RO starts at the same cycle τin (=τout) in the radiation image capturing apparatus 1, the continuing time of the charge accumulating state I (see C in drawing) is the same before and after switching the control mode. Therefore, the problem of having to wait for a few frames to a few tens of frames until the influence of the continuing time of the charge accumulating state I being long or short is cleared before starting the capturing does not occur. The operator is able to start the moving image capturing right after the control mode of the radiation image capturing apparatus 1 is switched from the internal synchronizing mode to the external synchronizing mode.

According to the present embodiment, as described above, the radiation image capturing apparatus 1 performs the process according to the internal synchronizing signal sin emitted in the radiation image capturing apparatus 1 until the control mode is switched to the external synchronizing mode. Therefore, the operator does not have to perform the operation or process such as connecting the radiation image capturing apparatus 1 to the control unit 60 in order to perform the pre-process such as the warmup reset in the radiation image capturing apparatus 1 and preprocess such as the warmup reset in the radiation image capturing apparatus 1 can be performed by simply turning on the power of the radiation image capturing apparatus 1 as usual.

Figures 11, 12:
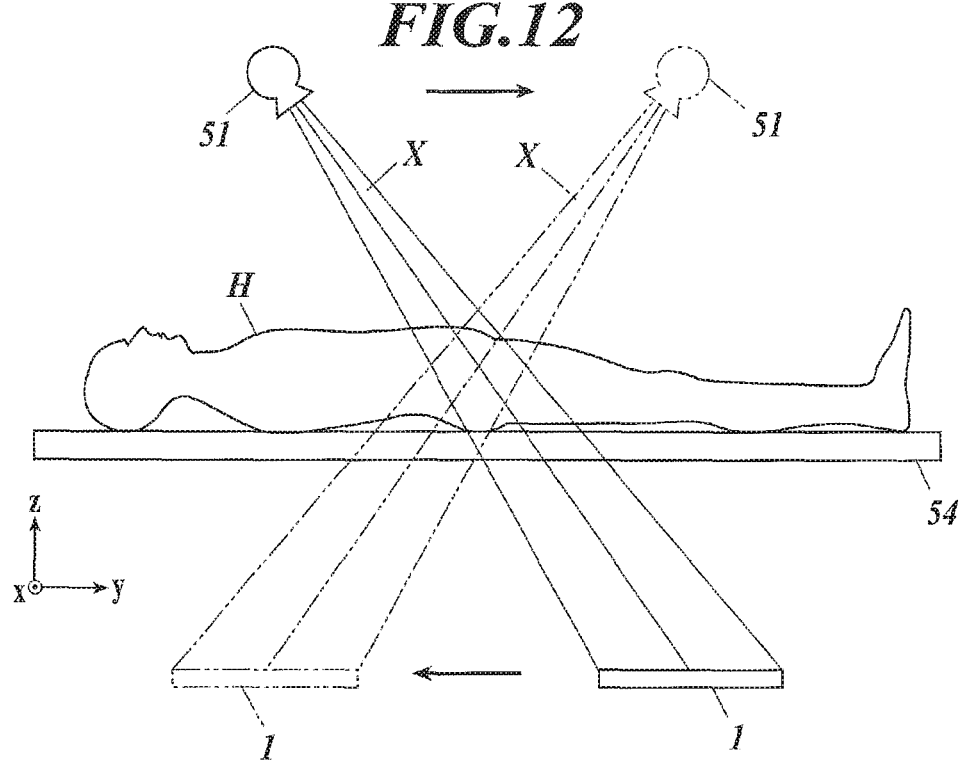
FIG. 11 is a diagram describing an example of how image data is extracted at a predetermined percentage from one frame of the read out image data.
FIG. 12 is a diagram describing a plurality of images are captured while the position of the radiation irradiating apparatus and the position of the radiation image capturing apparatus are changed with respect to the subject in tomosynthesis capturing.

Regarding the transfer (see FIG. 9) for each frame, the example of transferring the image data D, the offset data O, or the true image data D* is described. Alternatively, as shown in FIG. 11, the image data D can be extracted at a predetermined percentage (one for every four scanning lines in FIG. 11) from the image data D of one readout frame, and the extracted image data D (or the true image data D* corresponding to the above) can be transferred to the image processing apparatus 70.

Alternatively, for example, instead of extracting and transferring the image data D at a predetermined percentage from the image data D of one frame, the image data D of one frame for every predetermined number of frames can be extracted (that is, for example, one frame of image data D at a percentage of one frame for every three frames can be extracted) and transferred.

According to the above-described configuration, the time necessary for transfer becomes shorter in the amount that the data amount that is transferred from the radiation image capturing apparatus 1 to the image processing apparatus 70 for each frame (or percentage of one frame for every predetermined number of frames) becomes smaller and it is possible to shorten the time from when the data is transferred from the radiation image capturing apparatus 1 until the frame image is displayed on the display 71 of the image processing apparatus 70. Therefore, it is possible to display the frame images on the display 71 in real time.

Figure 13:
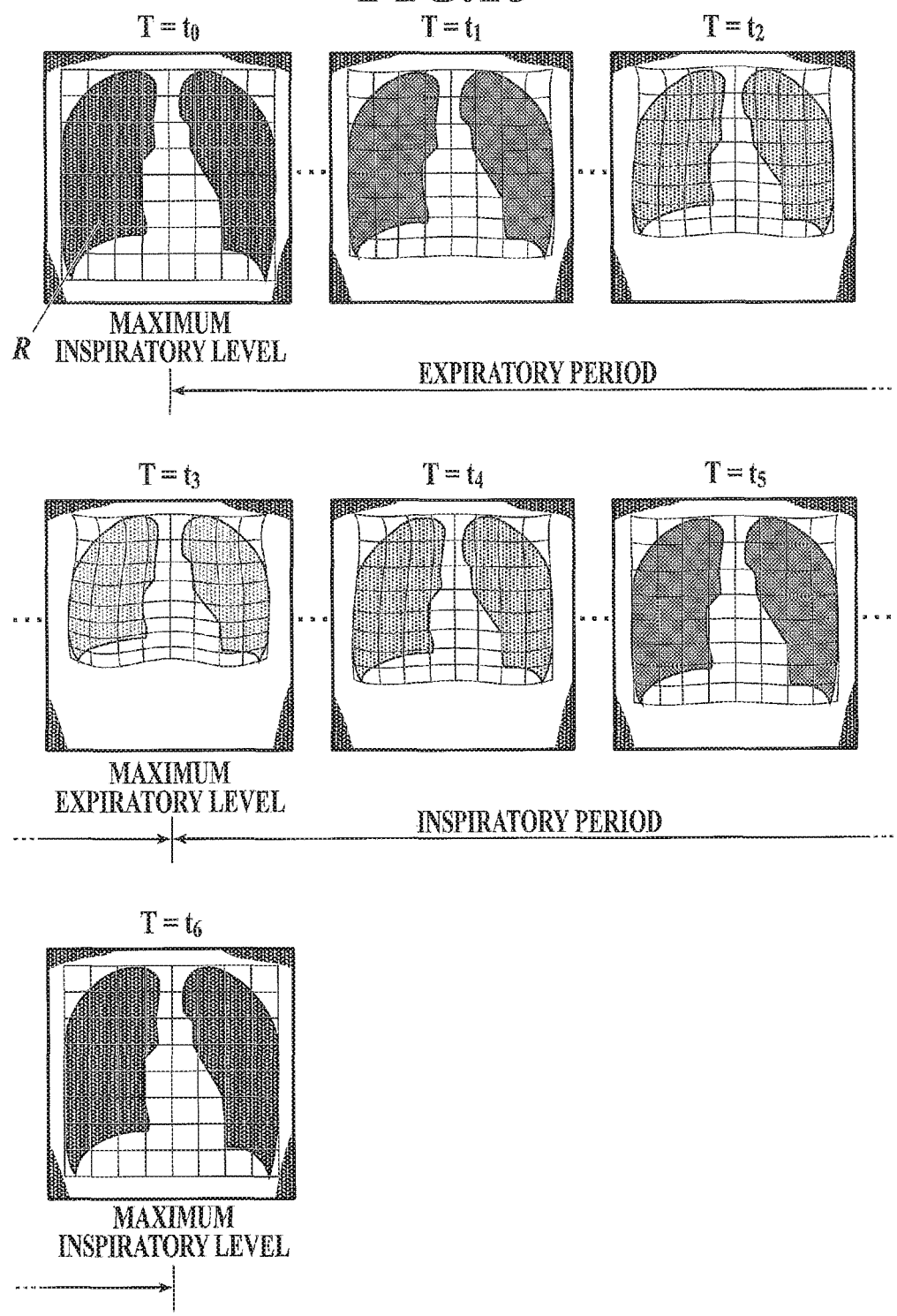
FIG. 13 is a diagram showing an example of frame images captured in movement capturing of a chest of a patient.

According to the present embodiment, the moving image capturing is capturing of the movement of the chest of the patient as shown in FIG. 13. The radiation image capturing system 100 according to the present embodiment is the radiation image capturing system in which the radiation is irradiated a plurality of times on the subject and the moving image capturing is performed. Therefore, the present invention can be applied to other radiation image capturing systems which perform capturing of movement. For example, it is possible to apply the present invention to tomosynthesis capturing as shown in FIG. 12. According to tomosynthesis capturing, as shown in FIG. 12, a plurality of radiation images (frame images) are captured while changing the irradiating position y51 and the irradiating angle of the radiation source 51 of the radiation irradiating apparatus 50 and the position y1 of the radiation image capturing apparatus 1 with respect to the subject H.

For example, from the viewpoint of irradiating radiation a plurality of times on the subject and performing capturing, for example, capturing using the method of dual energy subtraction, the radiation X is normally irradiated to the subject one time each changing the energy E (two times total) with the subject H standing as shown in FIG. 3 and the subject laid down as shown in FIG. 12.

The radiation image capturing system 100 according to the present embodiment can be applied to capturing using the tomosynthesis capturing and the dual energy subtraction. The radiation image capturing system 100 can be applied to any capturing which irradiates radiation on the subject a plurality of times to perform capturing.

The present invention is not limited to the above-described embodiment, and the present invention can be suitably changed without leaving the scope of the present invention.

What is claimed is:

1. A radiation image capturing system which performs moving image capturing by irradiating a subject with radiation a plurality of times, the radiation image capturing system comprising:
 a radiation image capturing apparatus which performs a readout process of image data from a plurality of radiation detecting elements aligned two-dimensionally,
 a radiation irradiating apparatus which irradiates the radiation image capturing apparatus through a subject with radiation from a radiation source according to control by a generator; and
 a control device which transmits an external synchronizing signal to the radiation image capturing apparatus, which transmits an irradiating request signal to the generator of the radiation irradiating apparatus, and which synchronizes the radiation image capturing apparatus with the radiation irradiating apparatus,
 wherein,
 the radiation image capturing apparatus switches between control modes, the control modes being an internal synchronizing mode which performs a process according to an internal synchronizing signal emitted in the apparatus and an external synchronizing mode which performs a process with reference to the external synchronizing signal transmitted from the control device;
 when the external synchronizing signal transmitted from the control device is received, the radiation image capturing apparatus switches the control mode from the internal synchronizing mode to the external synchronizing mode;
 after the control mode is switched, the radiation image capturing apparatus starts the readout process of the image data at a timing delayed a predetermined amount of time from a timing that the external synchronizing signal is received; and
 the control device transmits the irradiating request signal to the generator of the radiation irradiating apparatus at a timing delayed a predetermined amount of time from a timing that the irradiating request signal should be transmitted to the generator.

2. The radiation image capturing system according to claim 1, wherein, the predetermined amount of time is calculated as a difference subtracting from a cycle of the internal synchronizing signal a phase difference between the internal synchronizing signal right before the control mode is switched and the external synchronizing signal right after the control mode is switched.

3. The radiation image capturing system according to claim 1, wherein, the predetermined amount of time is calculated in the radiation image capturing apparatus and transmitted to the control device.

4. The radiation image capturing system according to claim 1, wherein, the radiation image capturing apparatus performs a warmup reset which is a reset process of the radiation detecting elements with a readout IC used in the readout process of the image data in a conducted state according to the internal synchronizing signal until the radiation image capturing apparatus switches the control mode from the internal synchronizing mode to the external synchronizing mode.

5. The radiation image capturing system according to claim 1, wherein, after the control mode is switched to the external synchronizing mode and before the radiation irradiating apparatus starts irradiating with the radiation, the radiation image capturing apparatus performs the readout process in a state in which irradiating with the radiation is not performed to readout offset data.

6. The radiation image capturing system according to claim 5, wherein, when the moving image capturing starts, the radiation image capturing apparatus transfers to an image processing apparatus a value subtracting the offset data for each radiation detecting element from the image data readout in the readout process each time the readout process of the image data is performed.

* * * * *